(12) United States Patent
Krause

(10) Patent No.: US 6,179,792 B1
(45) Date of Patent: Jan. 30, 2001

(54) ACOUSTIC WAVE THERAPY APPARATUS WITH REDUCED NOISE DURING ACOUSTIC WAVE EMISSION

(75) Inventor: Hartmut Krause, Erlangen (DE)

(73) Assignee: Siemens Aktiengesellschaft, Munich (DE)

( * ) Notice: Under 35 U.S.C. 154(b), the term of this patent shall be extended for 0 days.

(21) Appl. No.: 09/157,755

(22) Filed: Sep. 22, 1998

(30) Foreign Application Priority Data

Sep. 30, 1997 (DE) .............................................. 197 43 376

(51) Int. Cl.[7] ...................................................... A61H 1/00
(52) U.S. Cl. ................................... 601/2; 601/4; 381/71.1
(58) Field of Search ........................... 601/2–4; 600/439; 604/22; 381/71.1, 71.7, 71.8, 71.14; 367/147

(56) References Cited

U.S. PATENT DOCUMENTS

| | | | |
|---|---|---|---|
| 4,025,724 | 5/1977 | Davidson, Jr. et al. | |
| 4,489,441 | * 12/1984 | Chaplin | 381/71 |
| 4,985,925 | * 1/1991 | Langberg et al. | 381/72 |
| 5,267,320 | * 11/1993 | Fukumizu | 381/71 |
| 5,313,945 | * 5/1994 | Friedlander | 128/653.2 |
| 5,329,593 | * 7/1994 | Lazzeroni et al. | 381/357 |
| 5,394,786 | * 3/1995 | Gettle et al. | 86/50 |
| 5,427,102 | * 6/1995 | Shimode et al. | 128/653.2 |
| 5,444,786 | * 8/1995 | Raviv | 381/71 |
| 5,492,129 | * 2/1996 | Greenberger | 128/715 |
| 5,689,572 | * 11/1997 | Ohki et al. | 381/71.3 |

* cited by examiner

Primary Examiner—Marvin M. Lateef
Assistant Examiner—Shawna J. Shaw
(74) Attorney, Agent, or Firm—Schiff Hardin & Waite

(57) ABSTRACT

An acoustic wave therapy apparatus has an acoustic wave source such as shock wave source and an acoustic transmitter that emits such a separate acoustic signal that, during operation of the acoustic wave therapy apparatus, at least partial cancels the air-borne sound caused by the acoustic wave source.

8 Claims, 1 Drawing Sheet

ACOUSTIC WAVE THERAPY APPARATUS WITH REDUCED NOISE DURING ACOUSTIC WAVE EMISSION

BACKGROUND OF THE INVENTION

1. Field of the Invention

The present invention is directed to an acoustic wave therapy apparatus of the type employing an acoustic wave source.

2. Description of the Prior Art

Acoustic wave therapy apparatuses of the above type are utilized for a large variety of medical purposes. When shock waves are to be generated as acoustic waves, such apparatuses are employed, for example, for disintegrating calculi (lithotripsy) or for alleviating pain in joint-proximate soft tissue regions (pain therapy).

Given employment of such an acoustic wave therapy apparatus, the acoustic wave source produces substantial noise when it generates shock waves, that is considered disturbing by the medical personnel as well as by the patient.

SUMMARY OF THE INVENTION

An object of the present invention is to provide an acoustic wave therapy apparatus of the type initially described wherein irritation due to the air-borne sound caused by the operation of the acoustic wave source are at least reduced.

This object is inventively achieved in an acoustic wave therapy apparatus having an acoustic wave source, particularly a shock wave source, and a sound transmitter that emits a separate acoustic signal that produces a cancellation of the air-borne sound caused by the acoustic wave source during operation of the acoustic wave therapy apparatus.

In addition to the air-borne sound of the acoustic wave source, thus, the acoustic wave therapy apparatus in the case of the invention additionally emits an acoustic signal that interferes with the air-borne sound of the acoustic wave source in such a way that at least partial canceling of perceptible audio sensation ensues. A resultant signal thus arises whose acoustic pressure is lower than that of the air-borne sound caused by the acoustic wave source.

According to a first version of the invention, the acoustic signal emitted in addition to the air-borne sound of the acoustic wave source is acquired directly from the air-borne sound caused by the acoustic wave source. To this end, a sound sensor is provided for picking up the air-borne sound caused by the acoustic wave source, the output signal of this sound sensor being supplied via a signal processing circuit to an acoustic transmitter. In order to assure that the desired acoustic canceling occurs, the signal processing circuit can contain a phase shifter that gives the output signal of the acoustic sensor a phase shift such that the acoustic signal emitted by the acoustic transmitter is shifted in phase, preferably by 180°, relative to the air-borne sound caused by the acoustic wave source. Under certain circumstances, however, a phase shifter need not be used, namely when a phase shift already occurs in the signal path from the acoustic wave source via the acoustic sensor and the acoustic transmitter, resulting in a "natural" phase shift of the acoustic signal relative to the air-borne sound caused by the acoustic wave source that effects at least a partial acoustic canceling. Moreover, the signal processing circuit can include a filter with a filter characteristic selected such that only spectral components of the output signal of the acoustic sensor that are found to be particularly disturbing by human hearing proceed to the acoustic transmitter. It is assured in this way that an acoustic signal having an unnecessarily high acoustic power need not be emitted, but only that acoustic power that is required in order to achieve the desired effect.

In a further version of the invention the acoustic signal is not directly acquired from the air-borne sound caused by the acoustic wave source; rather, data corresponding to the acoustic signal are stored. In this case, the acoustic wave therapy apparatus has a memory and a digital-to-analog converter, whereby data are stored in the memory that correspond to (characterize) an acoustic signal which, given emission via the acoustic transmitter, causes a canceling of the air-borne sound emanating from the acoustic wave source. The data stored in the memory are supplied, during operation of the acoustic wave therapy apparatus, to the digital-to-analog converter when an acoustic wave is triggered and the analog output signal of the digital-to-analog converter is supplied to the acoustic transmitter. The data acquired in the memory can, for example, be acquired by registering the air-borne sound caused by the acoustic wave source with an acoustic sensor, and the output signal of the acoustic sensor is then digitized. The corresponding digital data can optionally be directly stored or can be modified in a suitable way before storage on the basis of digital signal processing, for example filtering and/or phase shifting.

Regardless of whether a complete or only a partial canceling of the air-borne sound caused by the acoustic wave source ensues, in an embodiment of the invention provides means are provided that, in addition to reproducing the acoustic signal serving the purpose of canceling the air-borne sound caused by the acoustic wave source, additionally allow the emission of a non-utilitarian audio signal with the acoustic transmitter (i.e., an acoustic signal performing a calming function). There is then the possibility, for example, of playing back music that is derived from an audio signal source such as a CD player.

DESCRIPTION OF THE PREFERRED EMBODIMENTS

Figure 1:
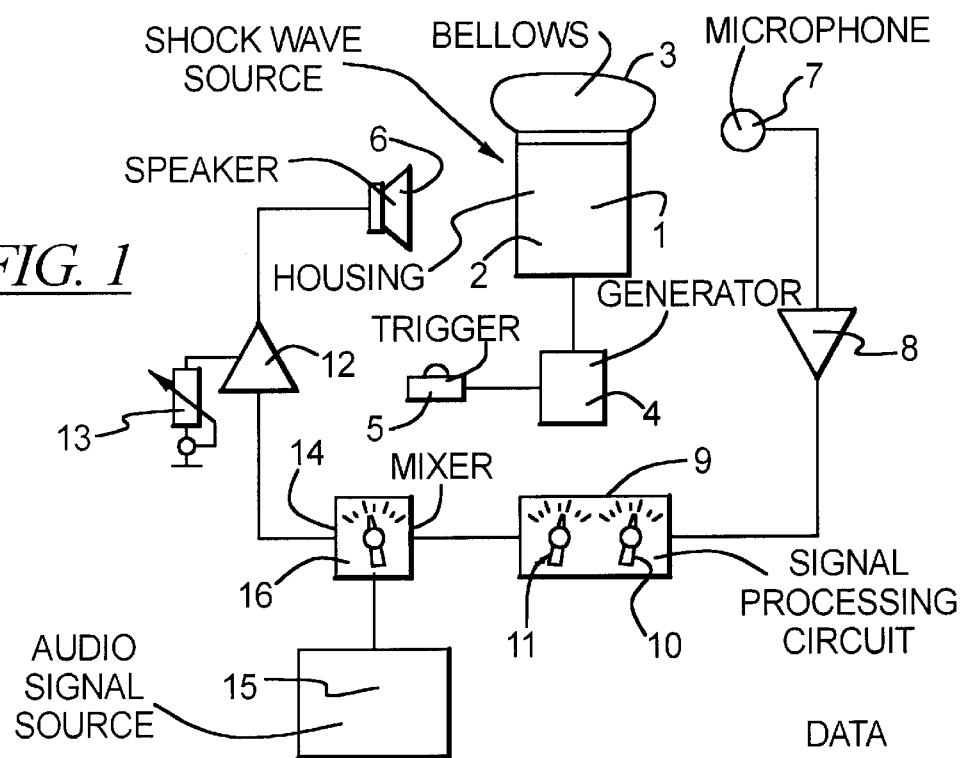
FIG. 1 is a schematic, block-circuit diagram illustration of an inventive acoustic wave therapy apparatus.

The inventive acoustic wave therapy apparatus includes a shock wave source 1 as the acoustic source which, for example, can be a known electro-hydraulic shock wave source, a piezo-electric shock wave source or an electro-magnetic shock wave source. The shock wave source 1 is preferably an electromagnetic shockwave source according to U.S. Pat. No. 4,674,505.

The shock wave source 1 has a housing 2 filled in its interior with a fluid as an acoustic propagation medium, and closed at its end provided for application to the body surface of a patient with a flexible coupling bellows 3 in which the fluid is likewise situated.

The shock wave source 1 is connected to an electrical generator 4 that charges the shock wave source 1 with high-intensity electrical pulses for generating shock waves.

The generator 4 is connected to a trigger key 5 upon actuation of which the generator 4 emits individual current pulses or sequences of current pulses, so that the shock wave source 1 accordingly emits individual shock waves or sequences of shock waves.

During the operation of such shock wave therapy apparatus, the shock wave source 1 produces not only the acoustic shock waves required for the treatment, but also the shock wave source 1 produces considerable noise that the medical personnel as well as the patient consider disturbing.

In order to reduce this irritation, the inventive shock wave therapy apparatus has an acoustic transmitter, such as a loudspeaker 6 in the case of the described exemplary embodiment, that emits an acoustic signal which, during operation of the shock wave therapy apparatus, produces at least a partial canceling of the air-borne sound caused by the shock wave source 1. The loudspeaker 6 can be an electro-acoustic transducer of an arbitrary type insofar as it is merely assured that it is capable of emitting acoustic signals with an adequate level in the frequency range perceived by human hearing.

The electrical signal for driving the loudspeaker 6 is acquired by a transmission chain given the shock wave therapy apparatus of FIG. 1, beginning with a microphone 7, as an acoustic sensor and ending with the loudspeaker 6. The microphone 7 serves the purpose of picking up the air-borne sound caused by the shock wave source 1. Its output signal is amplified by an amplifier 8 (which can be omitted) and is supplied to a signal processing circuit 9.

The signal processing circuit 9 contains a phase shifter that gives the output signal of the microphone 7 a phase shift such that the acoustic signal emitted by the loudspeaker 6 is phase shifted compared to the air-borne sound caused by the shock wave source. This phase shift can be set with a setting control and preferably amounts to at least approximately 180°.

The signal processing circuit 9 also contains a filter that has a filter characteristic so that only spectral components of the output signal of the microphone 7 that are found to be particularly disturbing by human hearing proceed to the loudspeaker 6. Thus an acoustic signal having an unnecessarily high acoustic power need not be emitted, but only a signal having acoustic power that is required in order to achieve the desired effect. At the same time, this relieves the loudspeaker 6. The filter characteristic in the described exemplary embodiment is variable, namely with a setting control 11.

The phase shifter and the filter of the signal processing circuit 9 are constructed in a conventional way.

From the signal processing circuit 9, the signal proceeds to an amplifier 12 whose gain in the described exemplary embodiment is variable, this being indicated by a potentiometer 13.

The loudspeaker 6 is connected to the output of the amplifier 12.

During operation of the shock wave therapy apparatus of FIG. 1, the air-borne sound caused by the shock wave source 1 is picked up with the microphone 7, and the output signal of the microphone 7 is edited by the amplifier 8 of the signal processing circuit 9 and the amplifier 12 so that the acoustic signal emitted by the loudspeaker 6 effects an at least partial canceling of the air-borne sound caused by the shock wave source 1, leading to a reduction of the aforementioned irritation.

The setting of the phase shift and the filter characteristic of the signal processing circuit 9 and the gain of the amplifier 12 ensues during operation of the shock wave therapy apparatus so that, based on the audio perceptions of persons present in the vicinity of the apparatus or given the assistance of an acoustic level meter, an optimal canceling of the air-borne sound caused by the shock wave source 1 is achieved.

Given the exemplary embodiment according to FIG. 1, means are provided that in addition to the playback of the acoustic signal serving the purpose of canceling the air-borne sound caused by the shock wave source 1, allow the emission of non-utilitarian audio signal. There is then the possibility of, for example, playing music in order to create a pleasant atmosphere both for the patient as well as for the medical personnel.

Given the exemplary embodiment according to FIG. 1, a mixer stage 14 is connected for this purpose into the signal path of the output signal of the microphone 7, this allowing a non-utilitarian audio signal derived from an audio signal source 15, for example a CD player to be mixed in. In order to be able to set the volume with which this non-utilitarian audio signal is played back, the mixer stage 14 has a level control 16.

Figure 2:
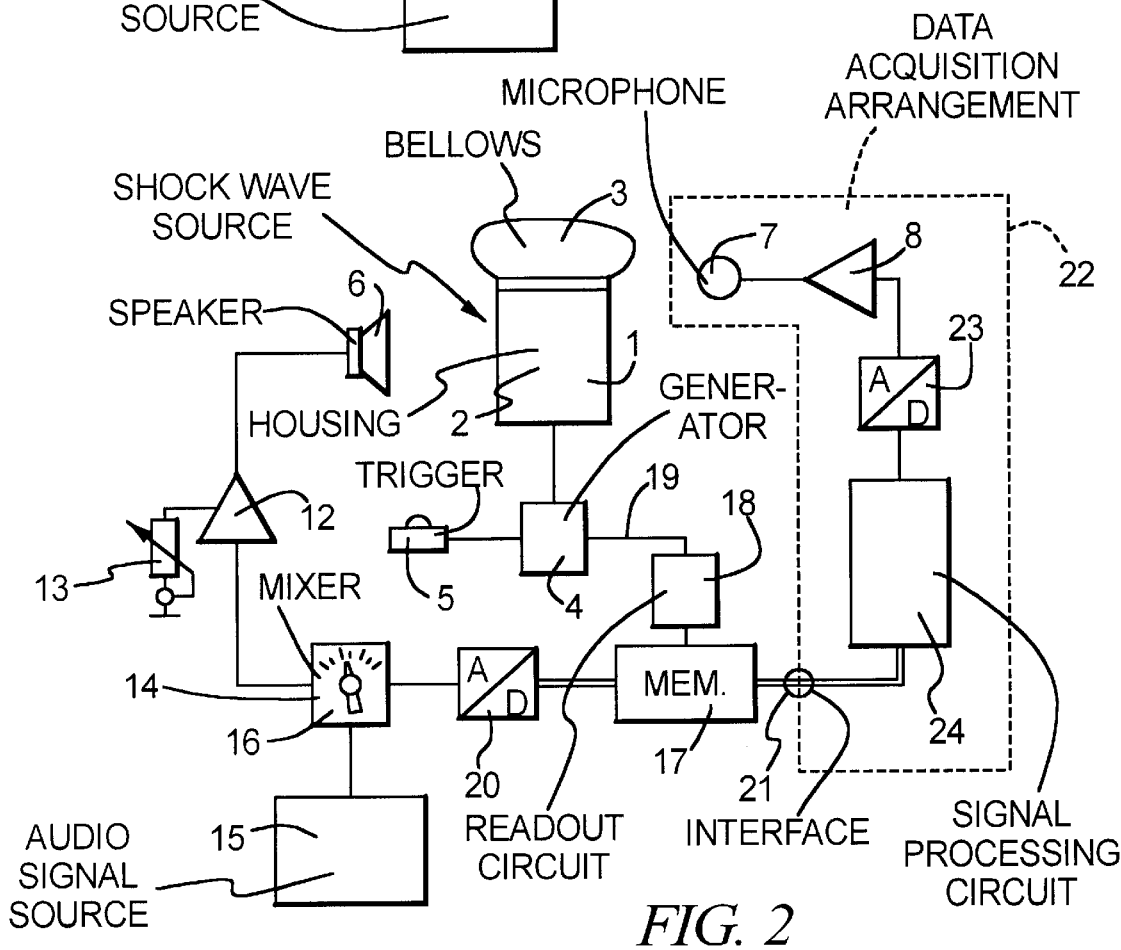
FIG. 2 shows a further embodiment of an inventive acoustic wave therapy apparatus in an illustration analogous to FIG. 1.

The exemplary embodiment according to FIG. 2 coincides with the above-described exemplary embodiment in terms of basic operation, for which reason respectively identical or substantially identical components have the same reference characters.

Whereas the electrical signal corresponding to the acoustic signal to be emitted by the loudspeaker 6 in the exemplary embodiment according to FIG. 1 is directly derived from the air-borne sound caused by the shock wave source 1 and picked up with the microphone 7, the exemplary embodiment according to FIG. 2 provides a memory 17 in which digital data are stored that are readout from the memory 17 with a read-out circuit 18 whenever the generator 4 drives the shock wave source 1 with a current pulse in order to generate a shock wave. The required coupling between the generator 4 and the read-out circuit 18 is produced via a trigger line 19.

The output data of the memory 17 proceed to a digital-to-analog converter 20. The analog output signal thereof proceeds via the mixer stage 14 and the amplifier 12 to the loudspeaker 6.

The data stored in the memory 17, which, for example, can be an erasable read-only memory, for example an EEPROM, are read into the memory 17 via a corresponding interface 21.

For example, the data can be acquired during a data acquisition procedure using a data acquisition arrangement 22 shown in FIG. 2.

The data acquisition arrangement 22 contains a microphone 7 for picking up the air-borne sound generated by the shock wave source 1. The output signal thereof proceeds via the amplifier 8 to an analog-to-digital converter 23 whose digital output data corresponding to the output signal of the microphone 7 are supplied to a digital signal processor unit 24 that, in a known way, effects the required phase shift and filter operations on the basis of digital signal processing. The digital signal processor 24 is programmable in a known way. For example, the data acquisition arrangement 22—except for the microphone 7—can be implemented as a plug-in card for a commercially obtainable personal computer, whereby the programming of the digital signal processor 24 then ensues in a known way with suitable software that is capable of running on the personal computer and that can partly even be commercially obtained.

During the data acquisition event, the digital output data of the digital signal processor unit 24 are supplied via the interface 21 to the memory 17. In the data acquisition procedure the phase shift with the digital signal processor unit 24 and/or the filter operations that are implemented are varied in steps and, following each step, the resulting data are read into the memory 17 and are checked in a test mode to determine to what extent the desired canceling effect occurs. When the desired result has been achieved, the data acquisition arrangement 22 can be disconnected from the interface 21; the most recent data read into the memory 17 are preserved for further operation.

The invention has been described above with reference to the example of shock wave therapy apparatus, however, it can also be employed with other acoustic wave therapy apparatus, for example those that contain a source of therapeutic ultrasound as the shock wave source that can emit continuously or in the form of a sequence of pulse packets, known as "bursts", that respectively cover a number of half-cycles.

Although modifications and changes may be suggested by those skilled in the art, it is the intention of the inventor to embody within the patent warranted hereon all changes and modifications as reasonably and properly come within the scope of his contribution to the art.

I claim as my invention:

1. An acoustic wave therapy apparatus comprising:

an acoustic wave source which emits a utilitarian acoustic wave accompanied by airborne sound said utilitarian acoustic wave having a medically therapeutic content;

an acoustic transmitter which emits an acoustic signal which, during emission of said acoustic wave by said acoustic wave source, at least partially cancels said air-borne sound without substantially disturbing said therapeutic content of said utilitarian acoustic wave.

2. An acoustic wave therapy apparatus as claimed in claim 1 further comprising an acoustic sensor which picks up said air-borne sound and which emits an output signal corresponding thereto, and a signal processing circuit connected to said acoustic sensor and to said acoustic transmitter for driving said acoustic transmitter dependent on said output signal of said sensor.

3. An acoustic wave therapy apparatus as claimed in claim 2 wherein said signal processing circuit contains a phase shifter which acts on said output signal of said sensor to produce a drive signal for said acoustic transmitter for causing said acoustic transmitter to emit said acoustic signal which is phase shifted compared to said air-borne sound.

4. An acoustic wave therapy apparatus as claimed in claim 3 wherein said phase shifter comprises at least a 180° phase shifter.

5. An acoustic wave therapy apparatus as claimed in claim 2 wherein said signal processing circuit comprises a filter which acts on said output signal of said acoustic sensor for producing a drive signal for said acoustic transmitter containing only spectral components of said output signal which are disturbing to human hearing.

6. An acoustic wave therapy apparatus as claimed in claim 1 further comprising:

a memory for storing digital data characterizing an acoustic signal which, when emitted by said acoustic transmitter, causes canceling of said air-borne sound;

a digital-to-analog converter connected between said memory and said acoustic transmitter for converting said digital data stored in said memory to an analog drive signal for operating said acoustic transmitter; and triggering means for causing said drive signal to be supplied to said acoustic transmitter upon emission of an acoustic wave by said acoustic wave source.

7. An acoustic wave therapy apparatus as claimed in claim 1 wherein said acoustic transmitter comprises means, in addition to emitting said acoustic signal for canceling said air-borne sound, emits a non-utilitarian audio signal.

8. An acoustic wave therapy apparatus as claimed in claim 1 wherein said acoustic wave source comprises a shock wave source.

* * * * *